United States Patent
Sinz

(10) Patent No.: US 10,197,555 B2
(45) Date of Patent: *Feb. 5, 2019

(54) METHOD OF SETTING A HANDOVER POSITION AND LABORATORY AUTOMATION SYSTEM

(71) Applicant: Roche Diagnostics Operations, Inc., Indianapolis, IN (US)

(72) Inventor: Achim Sinz, Waiblingen (DE)

(73) Assignee: Roche Diagnostics Operations, Inc.

( * ) Notice: Subject to any disclaimer, the term of this patent is extended or adjusted under 35 U.S.C. 154(b) by 54 days.

This patent is subject to a terminal disclaimer.

(21) Appl. No.: 15/613,596

(22) Filed: Jun. 5, 2017

(65) Prior Publication Data

US 2017/0363608 A1 Dec. 21, 2017

(30) Foreign Application Priority Data

Jun. 21, 2016 (EP) .................................... 16175566

(51) Int. Cl.
| | | |
|---|---|---|
| *G01N 35/04* | (2006.01) | |
| *G01N 33/487* | (2006.01) | |
| *F16K 31/00* | (2006.01) | |
| *B65G 54/02* | (2006.01) | |
| *G01N 35/00* | (2006.01) | |

(52) U.S. Cl.
CPC ......... *G01N 33/4875* (2013.01); *B65G 54/02* (2013.01); *F16K 31/004* (2013.01); *G01N 35/0099* (2013.01); *G01N 35/04* (2013.01); *G01N 2035/0406* (2013.01); *G01N 2035/0465* (2013.01); *G01N 2035/0477* (2013.01); *G01N 2035/0494* (2013.01)

(58) Field of Classification Search
None
See application file for complete search history.

(56) References Cited

U.S. PATENT DOCUMENTS

| | | |
|---|---|---|
| 3,273,727 A | 9/1966 | Rogers et al. |
| 3,653,485 A | 4/1972 | Donlon |
| 3,901,656 A | 8/1975 | Durkos et al. |
| 4,150,666 A | 4/1979 | Brush |
| 4,395,164 A | 7/1983 | Beltrop et al. |
| 4,544,068 A | 10/1985 | Cohen |
| 4,771,237 A | 9/1988 | Daley |
| 5,120,506 A | 6/1992 | Saito et al. |
| 5,295,570 A | 3/1994 | Grecksch et al. |
| 5,309,049 A | 5/1994 | Kawada et al. |
| 5,523,131 A | 6/1996 | Isaacs et al. |
| 5,530,345 A | 6/1996 | Murari et al. |
| 5,636,548 A | 6/1997 | Dunn et al. |
| 5,641,054 A | 6/1997 | Mori et al. |
| 5,651,941 A | 7/1997 | Stark et al. |
| 5,720,377 A | 2/1998 | Lapeus et al. |
| 5,735,387 A | 4/1998 | Polaniec et al. |
| 5,788,929 A | 8/1998 | Nesti |

(Continued)

FOREIGN PATENT DOCUMENTS

| | | |
|---|---|---|
| CN | 201045617 Y | 4/2008 |
| CN | 102109530 A | 6/2011 |

(Continued)

*Primary Examiner* — Kathryn Wright

(74) *Attorney, Agent, or Firm* — Roche Diagnostics Operations, Inc.

(57) ABSTRACT

A method of setting a handover position of a gripping device at a laboratory automation system is presented. A position of a position determining device held by the gripping device is detected using position sensors in order to determine the handover position. A laboratory automation system configured to perform such a method is also presented.

14 Claims, 4 Drawing Sheets

(56) References Cited

U.S. PATENT DOCUMENTS

| | | | |
|---|---|---|---|
| 6,045,319 A | 4/2000 | Uchida et al. |
| 6,062,398 A | 5/2000 | Thalmayr |
| 6,141,602 A | 10/2000 | Igarashi et al. |
| 6,151,535 A | 11/2000 | Ehlers |
| 6,184,596 B1 | 2/2001 | Ohzeki |
| 6,191,507 B1 | 2/2001 | Peltier et al. |
| 6,206,176 B1 | 3/2001 | Blonigan et al. |
| 6,255,614 B1 | 7/2001 | Yamakawa et al. |
| 6,260,360 B1 | 7/2001 | Wheeler |
| 6,279,728 B1 | 8/2001 | Jung et al. |
| 6,293,750 B1 | 9/2001 | Cohen et al. |
| 6,429,016 B1 | 8/2002 | McNeil |
| 6,444,171 B1 | 9/2002 | Sakazume et al. |
| 6,571,934 B1 | 6/2003 | Thompson et al. |
| 7,028,831 B2 | 4/2006 | Veiner |
| 7,078,082 B2 | 7/2006 | Adams |
| 7,122,158 B2 | 10/2006 | Itoh |
| 7,278,532 B2 | 10/2007 | Martin |
| 7,326,565 B2 | 2/2008 | Yokoi et al. |
| 7,425,305 B2 | 9/2008 | Itoh |
| 7,428,957 B2 | 9/2008 | Schaefer |
| 7,578,383 B2 | 8/2009 | Itoh |
| 7,597,187 B2 | 10/2009 | Bausenwein et al. |
| 7,850,914 B2 | 12/2010 | Veiner et al. |
| 7,858,033 B2 | 12/2010 | Itoh |
| 7,875,254 B2 | 1/2011 | Garton et al. |
| 7,939,484 B1 | 5/2011 | Loeffler et al. |
| 8,240,460 B1 | 8/2012 | Bleau et al. |
| 8,281,888 B2 | 10/2012 | Bergmann |
| 8,502,422 B2 | 8/2013 | Lykkegaard |
| 8,796,186 B2 | 8/2014 | Shirazi |
| 8,833,544 B2 | 9/2014 | Stoeckle et al. |
| 9,097,691 B2 | 8/2015 | Onizawa et al. |
| 9,187,268 B2 | 11/2015 | Denninger et al. |
| 9,211,543 B2 | 12/2015 | Ohga et al. |
| 9,239,335 B2 | 1/2016 | Heise et al. |
| 9,423,410 B2 | 8/2016 | Buehr |
| 9,423,411 B2 | 8/2016 | Riether |
| 9,567,167 B2 | 2/2017 | Sinz |
| 9,575,086 B2 | 2/2017 | Heise et al. |
| 9,593,970 B2 | 3/2017 | Sinz |
| 9,598,243 B2 | 3/2017 | Denninger et al. |
| 9,658,241 B2 | 5/2017 | Riether et al. |
| 9,664,703 B2 | 5/2017 | Heise et al. |
| 2002/0009391 A1 | 1/2002 | Marquiss et al. |
| 2003/0092185 A1 | 5/2003 | Qureshi et al. |
| 2004/0050836 A1 | 3/2004 | Nesbitt et al. |
| 2004/0084531 A1 | 5/2004 | Itoh |
| 2005/0061622 A1 | 3/2005 | Martin |
| 2005/0109580 A1 | 5/2005 | Thompson |
| 2005/0194333 A1 | 9/2005 | Veiner et al. |
| 2005/0196320 A1 | 9/2005 | Veiner et al. |
| 2005/0226770 A1 | 10/2005 | Allen et al. |
| 2005/0242963 A1 | 11/2005 | Oldham |
| 2005/0247790 A1 | 11/2005 | Itoh |
| 2005/0260101 A1 | 11/2005 | Nauck et al. |
| 2005/0271555 A1 | 12/2005 | Itoh |
| 2006/0000296 A1 | 1/2006 | Salter |
| 2006/0047303 A1 | 3/2006 | Ortiz et al. |
| 2006/0219524 A1 | 10/2006 | Kelly et al. |
| 2007/0116611 A1 | 5/2007 | DeMarco |
| 2007/0210090 A1 | 9/2007 | Sixt et al. |
| 2007/0248496 A1 | 10/2007 | Bondioli et al. |
| 2007/0276558 A1 | 11/2007 | Kim |
| 2008/0012511 A1 | 1/2008 | Ono |
| 2008/0029368 A1 | 2/2008 | Komori |
| 2008/0056328 A1 | 3/2008 | Rund et al. |
| 2008/0131961 A1 | 6/2008 | Crees et al. |
| 2009/0004732 A1 | 1/2009 | LaBarre et al. |
| 2009/0022625 A1 | 1/2009 | Lee et al. |
| 2009/0081771 A1 | 3/2009 | Breidford et al. |
| 2009/0128139 A1 | 5/2009 | Drenth et al. |
| 2009/0142844 A1 | 6/2009 | Le Comte |
| 2009/0180931 A1 | 7/2009 | Silbert et al. |
| 2009/0322486 A1 | 12/2009 | Gerstel |
| 2010/0000250 A1 | 1/2010 | Sixt |
| 2010/0152895 A1 | 6/2010 | Dai |
| 2010/0175943 A1 | 7/2010 | Bergmann |
| 2010/0186618 A1 | 7/2010 | King et al. |
| 2010/0255529 A1 | 10/2010 | Cocola et al. |
| 2010/0300831 A1 | 12/2010 | Pedrazzini |
| 2010/0312379 A1 | 12/2010 | Pedrazzini |
| 2011/0050213 A1 | 3/2011 | Furukawa |
| 2011/0124038 A1 | 5/2011 | Bishop et al. |
| 2011/0172128 A1 | 7/2011 | Davies et al. |
| 2011/0186406 A1 | 8/2011 | Kraus et al. |
| 2011/0287447 A1 | 11/2011 | Norderhaug et al. |
| 2012/0037696 A1 | 2/2012 | Lavi |
| 2012/0129673 A1 | 5/2012 | Fukugaki et al. |
| 2012/0178170 A1 | 7/2012 | Van Praet |
| 2012/0211645 A1 | 8/2012 | Tullo et al. |
| 2012/0275885 A1 | 11/2012 | Furrer et al. |
| 2012/0282683 A1 | 11/2012 | Mototsu |
| 2012/0295358 A1 | 11/2012 | Ariff et al. |
| 2012/0310401 A1 | 12/2012 | Shah |
| 2013/0034410 A1 | 2/2013 | Heise et al. |
| 2013/0126302 A1 | 5/2013 | Johns et al. |
| 2013/0153677 A1 | 6/2013 | Leen et al. |
| 2013/0180824 A1 | 7/2013 | Kleinikkink et al. |
| 2013/0263622 A1 | 10/2013 | Mullen |
| 2013/0322992 A1 | 12/2013 | Pedrazzini |
| 2014/0170023 A1 | 6/2014 | Saito et al. |
| 2014/0234949 A1 | 8/2014 | Wasson et al. |
| 2015/0014125 A1 | 1/2015 | Hecht |
| 2015/0166265 A1 | 6/2015 | Pollack et al. |
| 2015/0241457 A1 | 8/2015 | Miller |
| 2015/0273468 A1 | 10/2015 | Croquette et al. |
| 2015/0273691 A1 | 10/2015 | Pollack |
| 2015/0276775 A1 | 10/2015 | Mellars et al. |
| 2015/0276776 A1 | 10/2015 | Riether |
| 2015/0276777 A1 | 10/2015 | Riether et al. |
| 2015/0276778 A1 | 10/2015 | Riether et al. |
| 2015/0276782 A1 | 10/2015 | Riether |
| 2016/0003859 A1 | 1/2016 | Wenczel et al. |
| 2016/0025756 A1 | 1/2016 | Pollack et al. |
| 2016/0054341 A1 | 2/2016 | Edelmann |
| 2016/0077120 A1 | 3/2016 | Riether |
| 2016/0097786 A1 | 4/2016 | Malinowski et al. |
| 2016/0229565 A1 | 8/2016 | Margner |
| 2016/0274137 A1 | 9/2016 | Baer |
| 2016/0282378 A1 | 9/2016 | Malinowski et al. |
| 2016/0341750 A1 | 11/2016 | Sinz et al. |
| 2016/0341751 A1 | 11/2016 | Huber et al. |
| 2017/0059599 A1 | 3/2017 | Riether |
| 2017/0096307 A1 | 4/2017 | Mahmudimanesh et al. |
| 2017/0097372 A1 | 4/2017 | Heise et al. |
| 2017/0101277 A1 | 4/2017 | Malinowski |
| 2017/0108522 A1 | 4/2017 | Baer |
| 2017/0131307 A1 | 5/2017 | Pedain |
| 2017/0131309 A1 | 5/2017 | Pedain |
| 2017/0131310 A1 | 5/2017 | Volz et al. |
| 2017/0138971 A1 | 5/2017 | Heise et al. |
| 2017/0160299 A1 | 6/2017 | Schneider et al. |
| 2017/0168079 A1 | 6/2017 | Sinz |
| 2017/0174448 A1 | 6/2017 | Sinz |
| 2017/0184622 A1 | 6/2017 | Sinz et al. |
| 2017/0248623 A1 | 8/2017 | Kaeppeli et al. |
| 2017/0248624 A1 | 8/2017 | Kaeppeli et al. |
| 2018/0067141 A1 | 3/2018 | Mahmudimanesh et al. |
| 2018/0074087 A1 | 3/2018 | Heise et al. |
| 2018/0106821 A1 | 4/2018 | Vollenweider et al. |
| 2018/0156835 A1 | 6/2018 | Hassan |
| 2018/0188280 A1 | 7/2018 | Malinowski |
| 2018/0210000 A1 | 7/2018 | van Mierlo |
| 2018/0210001 A1 | 7/2018 | Reza |
| 2018/0217174 A1 | 8/2018 | Malinowski |
| 2018/0217176 A1 | 8/2018 | Sinz et al. |
| 2018/0224476 A1 | 8/2018 | Birrer et al. |

FOREIGN PATENT DOCUMENTS

| | | |
|---|---|---|
| DE | 3909786 A1 | 9/1990 |
| DE | 102012000665 A1 | 8/2012 |

(56) References Cited

FOREIGN PATENT DOCUMENTS

| | | |
|---|---|---|
| DE | 102011090044 A1 | 7/2013 |
| EP | 0601213 A1 | 10/1992 |
| EP | 0775650 A1 | 5/1997 |
| EP | 0916406 A2 | 5/1999 |
| EP | 1122194 A1 | 8/2001 |
| EP | 1524525 A1 | 4/2005 |
| EP | 2119643 A1 | 11/2009 |
| EP | 2148117 A1 | 1/2010 |
| EP | 2327646 A1 | 6/2011 |
| EP | 2447701 A2 | 5/2012 |
| EP | 2500871 A1 | 9/2012 |
| EP | 2502675 B1 | 2/2014 |
| EP | 2887071 A1 | 6/2015 |
| GB | 2165515 A | 4/1986 |
| JP | S56-147209 A | 11/1981 |
| JP | 60-223481 A | 11/1985 |
| JP | 61-081323 A | 4/1986 |
| JP | S61-069604 A | 4/1986 |
| JP | S61-094925 A | 5/1986 |
| JP | S61-174031 A | 8/1986 |
| JP | S61-217434 A | 9/1986 |
| JP | S62-100161 A | 5/1987 |
| JP | S63-31918 A | 2/1988 |
| JP | S63-48169 A | 2/1988 |
| JP | S63-82433 U | 5/1988 |
| JP | S63-290101 A | 11/1988 |
| JP | 1148966 A | 6/1989 |
| JP | H01-266860 A | 10/1989 |
| JP | H02-87903 A | 3/1990 |
| JP | 03-112393 A | 5/1991 |
| JP | 03-192013 A | 8/1991 |
| JP | H03-38704 Y2 | 8/1991 |
| JP | H04-127063 A | 4/1992 |
| JP | H05-69350 A | 3/1993 |
| JP | H05-142232 A | 6/1993 |
| JP | H05-180847 A | 7/1993 |
| JP | 06-26808 A | 2/1994 |
| JP | H06-148198 A | 5/1994 |
| JP | 06-156730 A | 6/1994 |
| JP | 06-211306 A | 8/1994 |
| JP | 07-228345 A | 8/1995 |
| JP | 07-236838 A | 9/1995 |
| JP | H07-301637 A | 11/1995 |
| JP | H09-17848 A | 1/1997 |
| JP | H11-083865 A | 3/1999 |
| JP | H11-264828 A | 9/1999 |
| JP | H11-304812 A | 11/1999 |
| JP | H11-326336 A | 11/1999 |
| JP | 2000-105243 A | 4/2000 |
| JP | 2000-105246 A | 4/2000 |
| JP | 2001-124786 A | 5/2001 |
| JP | 2001-240245 A | 9/2001 |
| JP | 2005-001055 A | 1/2005 |
| JP | 2005-249740 A | 9/2005 |
| JP | 2006-106008 A | 4/2006 |
| JP | 2007-309675 A | 11/2007 |
| JP | 2007-314262 A | 12/2007 |
| JP | 2007-322289 A | 12/2007 |
| JP | 2009-036643 A | 2/2009 |
| JP | 2009-062188 A | 3/2009 |
| JP | 2009-145188 A | 7/2009 |
| JP | 2009-300402 A | 12/2009 |
| JP | 2010-243310 A | 10/2010 |
| JP | 2013-172009 A | 2/2013 |
| JP | 2013-190400 A | 9/2013 |
| SU | 685591 A1 | 9/1979 |
| WO | 1996/036437 A1 | 11/1996 |
| WO | 2003/042048 A3 | 5/2003 |
| WO | 2007/024540 A1 | 3/2007 |
| WO | 2008/133708 A1 | 11/2008 |
| WO | 2009/002358 A1 | 12/2008 |
| WO | 2010/042722 A1 | 4/2010 |
| WO | 2012/170636 A1 | 7/2010 |
| WO | 2010/087303 A1 | 8/2010 |
| WO | 2010/129715 A1 | 11/2010 |
| WO | 2012/158520 A1 | 11/2012 |
| WO | 2012/158541 A1 | 11/2012 |
| WO | 2013/152089 A1 | 10/2013 |
| WO | 2013/169778 A1 | 11/2013 |
| WO | 2013/177163 A1 | 11/2013 |
| WO | 2014/059134 A1 | 4/2014 |
| WO | 2014/071214 A1 | 5/2014 |

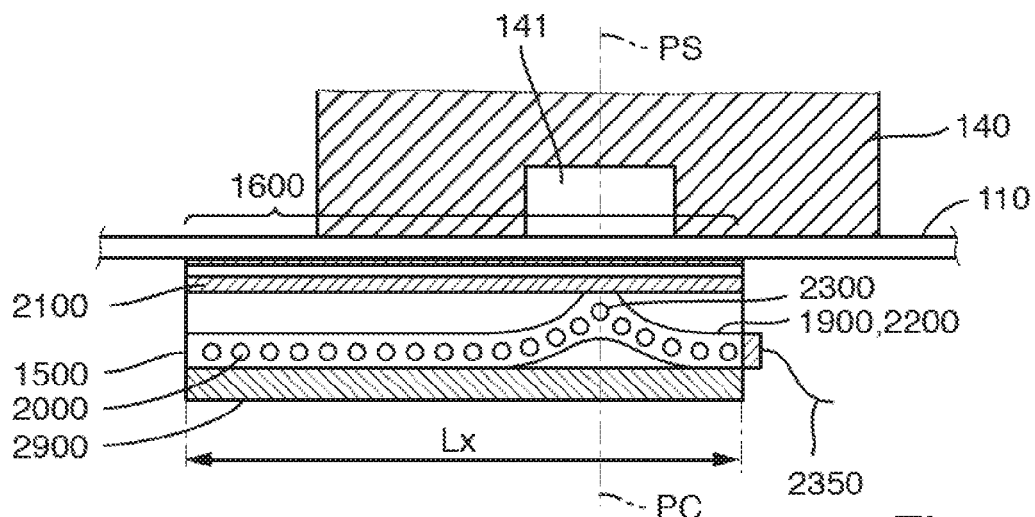
Fig. 4
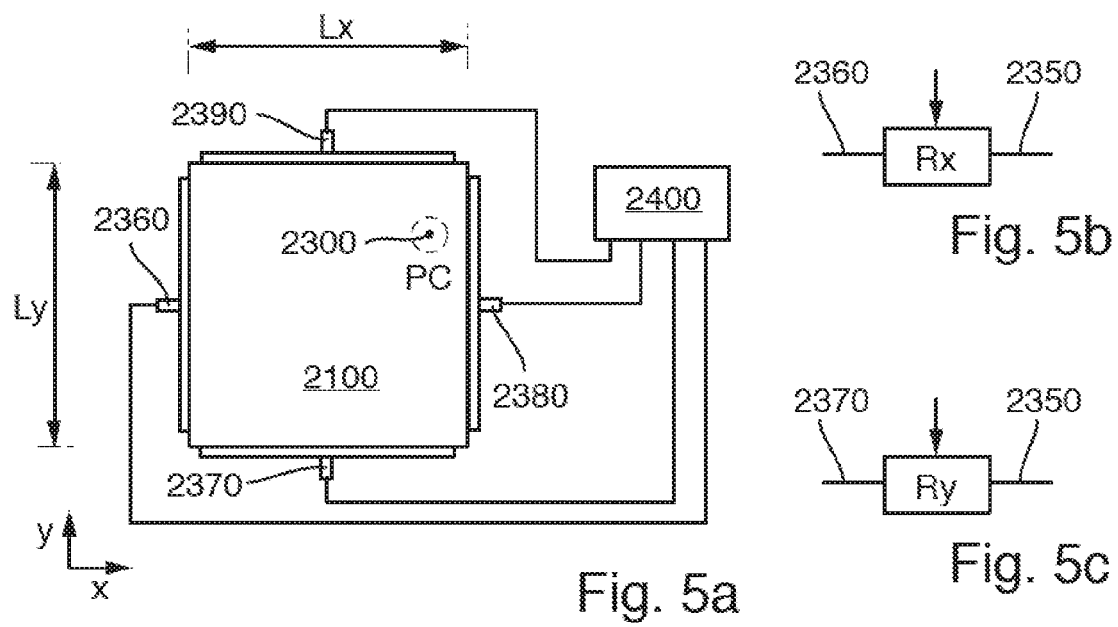
Fig. 5a
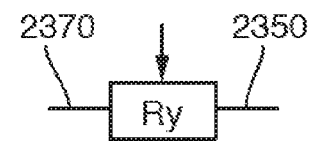
Fig. 5b
Fig. 5c
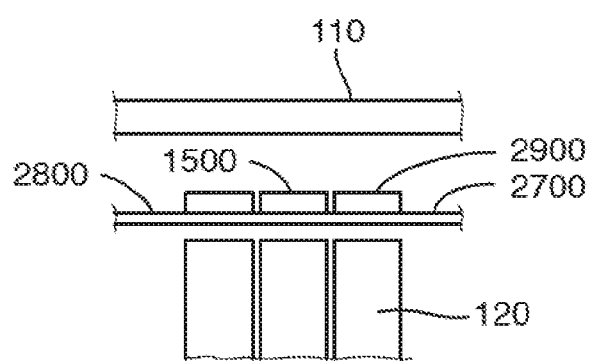
Fig. 6

METHOD OF SETTING A HANDOVER POSITION AND LABORATORY AUTOMATION SYSTEM

CROSS-REFERENCE TO RELATED APPLICATIONS

This application is a continuation of EP 16175566.5, filed Jun. 21, 2016, which is hereby incorporated by reference.

BACKGROUND

The present disclosure generally relates to a method of setting a handover position of a gripping device, which may be used in conjunction with a laboratory automation system. The present disclosure relates further to a laboratory automation system being configured to perform such a method.

Gripping devices are often used in laboratory automation systems, especially in order to place sample containers into sample container carriers movable on a transport plane, and in order to remove sample containers from such sample container carriers.

Known laboratory sample distribution systems are typically used in laboratory automation systems in order to transport samples contained in sample containers between different laboratory stations. A laboratory sample distribution system can provide for a high throughput and for reliable operation.

Typically, an internal coordinate system of the gripping device differs from an internal coordinate system of the laboratory sample distribution system. This means that a handover position, typically a position on which a sample container carrier has to be placed in order to be handled by the gripping device, has to be taught. This typically implies that that the different coordinate systems are aligned with one another.

Therefore, there is a need for a method of setting a handover position of a gripping device that is reliable and is easy to implement.

SUMMARY

According to the present disclosure, a method of setting a handover position of a gripping device is presented. The gripping device can be assigned to a laboratory sample distribution system having a transport plane, a number of electro-magnetic actuators positioned below the transport plane and a number of position sensors distributed over the transport plane. The handover position can be assigned to a handover electro-magnetic actuator. The method can comprise gripping, by the gripping device, a position determining device such that the position determining device is held fixedly by the gripping device. The position determining device can comprise a magnetically active device. The method can also comprise positioning the position determining device, while held by the gripping device, on the transport plane, detecting a first position of the position determining device on the transport plane using the position sensors, and setting the handover position based at least in part on the first position.

Accordingly, it is a feature of the embodiments of the present disclosure to provide for a method of setting a handover position of a gripping device that is reliable and is easy to implement. Other features of the embodiments of the present disclosure will be apparent in light of the description of the disclosure embodied herein.

BRIEF DESCRIPTION OF THE SEVERAL VIEWS OF THE DRAWINGS

The following detailed description of specific embodiments of the present disclosure can be best understood when read in conjunction with the following drawings, where like structure is indicated with like reference numerals and in which:

FIG. 4 illustrates a longitudinal section view of a sample container carrier, a transport plane and a position sensor of FIG. 3 according to an embodiment of the present disclosure.

FIG. 5a illustrates a cross section view of the position sensor of FIG. 4 according to an embodiment of the present disclosure.

FIG. 5b illustrates an electronic symbol for the position sensor of FIG. 4 in a first direction according to an embodiment of the present disclosure.

FIG. 5c illustrates another electronic symbol for the position sensor of FIG. 4 in a second direction according to an embodiment of the present disclosure.

FIG. 6 illustrates a longitudinal section view of the laboratory sample distribution system of FIG. 3 according to an embodiment of the present disclosure.

DETAILED DESCRIPTION

Figure 1:
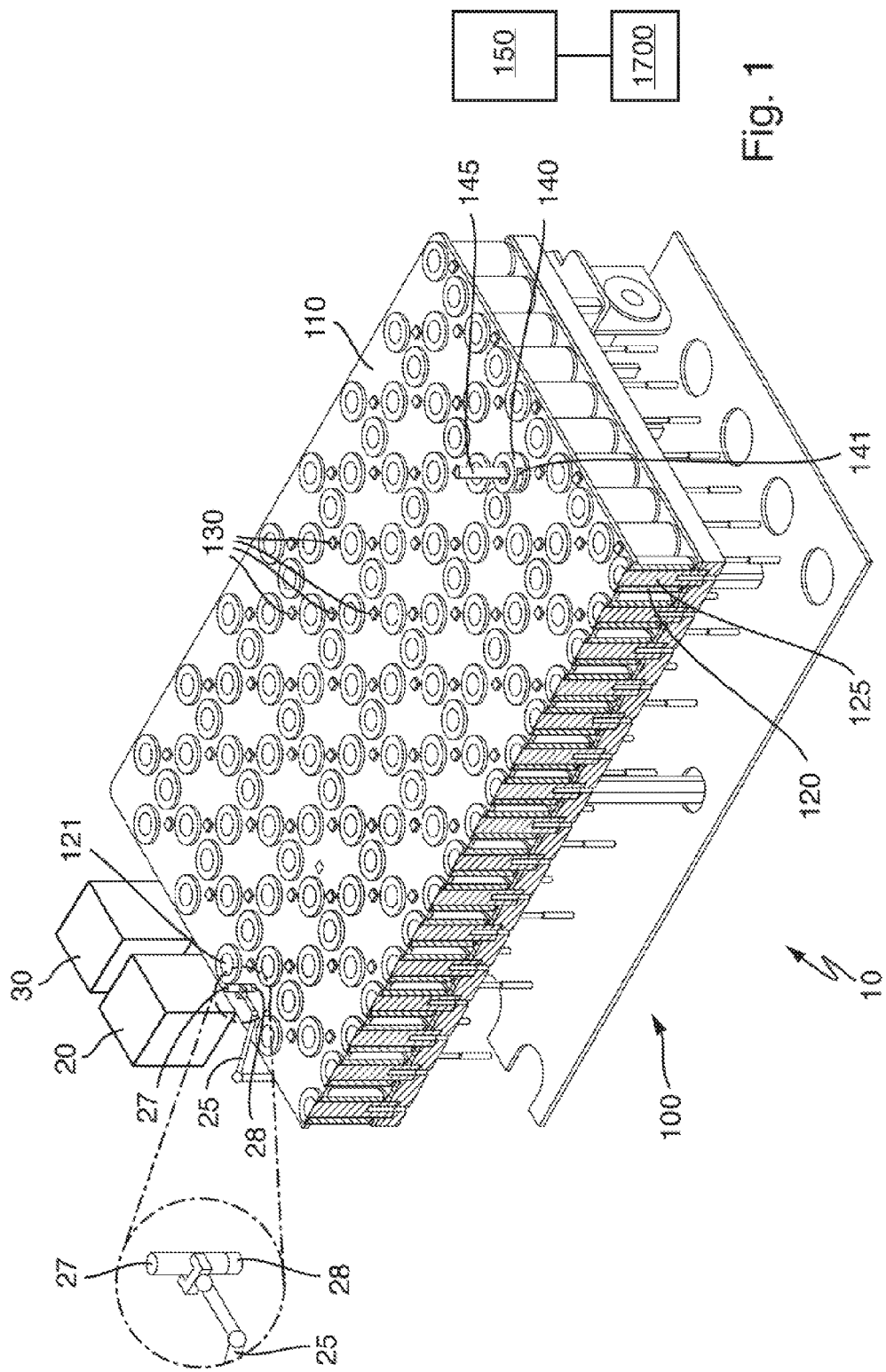
FIG. 1 illustrates a laboratory automation system according to an embodiment of the present disclosure.

In the following detailed description of the embodiments, reference is made to the accompanying drawings that form a part hereof, and in which are shown by way of illustration, and not by way of limitation, specific embodiments in which the disclosure may be practiced. It is to be understood that other embodiments may be utilized and that logical, mechanical and electrical changes may be made without departing from the spirit and scope of the present disclosure.

A method of setting a handover position of a gripping device is presented. The gripping device can be assigned to a laboratory sample distribution system having a transport plane, a number (e.g. 64 to 64000) of electro-magnetic actuators positioned below the transport plane and a number (e.g. 64 to 64000) of position sensors distributed over the transport plane, e.g. in the form of magnetic sensors (e.g. Hall sensors). The position sensors can be arranged in rows and columns under the transport plane. Accordingly, the electro-magnetic actuators can be arranged in rows and columns under the transport plane.

The handover position can be assigned to a handover electro-magnetic actuator. The handover electro-magnetic actuator can typically be one of the number of electro-magnetic actuators. The handover position can typically be a position at which the gripping device grips a sample container contained in or carried by a sample container carrier movably arranged on the transport plane, or at which the gripping device hands over or inserts a sample container to/into a sample container carrier.

The method can comprise the following step: grabbing or gripping, by the gripping device, a position determining device such that the position determining device can be held fixedly by the gripping device. The position determining device can comprise a magnetically active device, e.g. in form of a permanent magnet. The method can comprise the following steps: positioning the position determining device, while held by the gripping device, on the transport plane, detecting a first position of the position determining device on the transport plane using the position sensors, and setting the handover position based at least in part on the first position. It can be possible to determine a handover position in a fast and efficient manner. Manual operation is generally not necessary in order to perform this method.

According to an embodiment, the handover position can be set and represented in a coordinate system of the gripping device. Typically, this can correspond to a coordinate system used by a control device of the gripping device.

According to an embodiment, the handover position can be calculated based on a difference between the first position and a center position of the handover electro-magnetic actuator. This can allow for an easy calculation.

According to an embodiment, the position sensors can be configured to measure a quantitative strength of a magnetic field generated (caused) by the magnetically active device of the positioning determining device. This can allow a position determination having a high resolution, especially compared with position sensors giving only binary signals.

Typically, the position sensors can further be configured to measure a quantitative strength of a magnetic field generated by a respective magnetically active device of a sample container carrier.

According to an embodiment, the first position can be determined based on the strengths of the magnetic field measured by some or all of the position sensors.

According to an embodiment, for detecting the first position (only) position sensors surrounding the handover electro-magnetic actuator can be used. In other words, the first position can be determined based on the strengths of the magnetic field measured by position sensors surrounding the handover electro-magnetic actuator as well as the sensor at the handover position itself.

According to an embodiment, the electro-magnetic actuators can be deactivated while performing the method. This can avoid that the measurement is disturbed by magnetic fields generated (caused) by the electro-magnetic actuators.

According to an embodiment, the first position and/or the center position can be represented by planar (Cartesian) coordinates on the transport plane. Such planar coordinates can be well suited because most transport planes have a rectangular shape. However, it should be noted that also other types of coordinates, for example circular coordinates, can be used.

According to an embodiment, the step of positioning, by the gripping device, the position determining device on the transport plane can be performed such that the gripping device can be positioned over, or besides, the handover electro-magnetic actuator. This can allow for a small and exactly measurable distance between the handover electro-magnetic actuator and the position determining device.

According to an embodiment, positioning the position determining device, while being held by the gripping device, on the transport plane can be performed automatically. The automatic positioning can place the position determining device at a predefined or assumed handover position.

According to an embodiment, the position determining device can comprise a number of rolls, or ball-bearings, for contacting the transport plane. This can reduce friction between the position determining device and the transport plane.

According to an embodiment, the position determining device can comprise a metallic, or ferromagnetic, guide for guiding magnetic field lines generated by the magnetically active device towards the transport plane. This measure can lead to an increased magnetic field strength at the position sensors, leading to a more reliable measurement.

According to an embodiment, after determining the handover position, the method can comprises the following steps: positioning the position determining device, while being held by the gripping device, on the transport plane at the previously determined handover position, detecting a second position of the position determining device on the transport plane using the position sensors, and refining the handover position based at least in part on the second position.

This can lead to a further refinement of the determined handover position. It should be noted that these steps or similar steps can be repeated a plurality of times in order to further refine the handover position.

A laboratory automation system comprising a number (e.g. 1 to 100) of gripping devices and a laboratory sample distribution system is presented. The laboratory sample distribution system can comprise a number (e.g. 1 to 10000) of sample container carriers adapted to carry one or more sample containers, each sample container carrier comprising at least one magnetically active device, e.g. a permanent magnet. The laboratory sample distribution system can comprise a transport plane adapted to support the sample container carriers.

The laboratory sample distribution system can further comprise a number (e.g. 64 to 64000) of electro-magnetic actuators, stationary arranged below the transport plane. The electro-magnetic actuators can be adapted to move a sample container carrier on top of the transport plane by applying a magnetic force to the sample container carrier.

The laboratory sample distribution system can further comprise a control device configured to control the movement of the sample container carriers on top of the transport plane by driving the electro-magnetic actuators such that the sample container carriers move along corresponding transport paths.

For each gripping device, a handover electro-magnetic actuator can be assigned out of the number of electro-magnetic actuators. A sample container can be handed over to or from the respective gripping device while a sample container carrier carrying the respective sample container can be positioned above the handover electro-magnetic actuator.

The laboratory automation system can further comprise a process control unit. The process control unit can be configured to control the gripping device and the laboratory sample distribution system such that the above method can be performed. With regard to the method, all embodiments and variations disclosed herein can be applied. The process control unit and the control device may be identical, but may also be separate devices.

According to an embodiment, the magnetically active device of the position determining device may generate a stronger magnetic field than each of the magnetically active devices of the sample container carriers. This can lead to a strong magnetic field for the purpose of position determination, which leads to a more reliable measurement.

According to an embodiment, the laboratory automation system can comprise a number (e.g. 1 to 100) of laboratory stations. The laboratory stations can be pre-analytical, analytical and/or post-analytical stations. The laboratory sample distribution system may be adapted to transport the sample container carriers and/or sample containers between the laboratory stations. The laboratory stations may be arranged adjacent to the laboratory sample distribution system.

Pre-analytical stations may be adapted to perform any kind of pre-processing of samples, sample containers and/or sample container carriers.

Analytical stations may be adapted to use a sample or part of the sample and a reagent to generate a measuring signal, the measuring signal indicating if and in which concentration, if any, an analyte exists.

Post-analytical stations may be adapted to perform any kind of post-processing of the samples, sample containers and/or sample container carriers.

The pre-analytical, analytical and/or post-analytical stations may comprise at least one of a decapping station, a recapping station, an aliquot station, a centrifugation station, an archiving station, a pipetting station, a sorting station, a tube type identification station, a sample quality determining station, an add-on buffer station, a liquid level detection station, and a sealing/desealing station.

The number of position sensors may be stationary arranged below the transport plane. A position sensor may have a sensing region and an electrical resistance. The electrical resistance can be dependent on a position of a sample container carrier on the transport plane located in the sensing region. The laboratory sample distribution system may comprise a position determination unit. The position determination unit can be adapted to determine the positions of the sample container carriers on top of the transport plane by evaluating the electrical resistances of the position sensors.

The position sensors and the position determination unit can enable improved sample container carrier position detection on the transport plane. The sensing region may extend only in one direction or in one dimension on the transport plane and/or may comprise a sensing line or sensing stripe on the transport plane. Then, the position sensor may have only the one electrical resistance with its value in the one direction. Alternatively, the sensing region may extend in two directions being different from each other or in two dimensions on the transport plane and/or may comprise a sensing area on the transport plane. Then, the position sensor may have the one electrical resistance with two values in the two directions. In other words, the position sensor may have two electrical resistances each with a value in its direction. The sensing region may be limited, such that, when the sample container carrier may be located out or outside of the sensing region, the electrical resistance may not be dependent on the position of the sample container carrier on the transport plane. In this case, the electrical resistance may have a default value, e.g. a zero value or an extreme value. The electrical resistance and its values, respectively, may be unambiguously assigned or correlated to the position of the sample container carrier on the transport plane located in the sensing region. Hence, the position of the sample container carrier on the transport plane located in the sensing region may be unambiguously determined by the position determination unit. This can be an advantage to a Hall-sensor, which in contrast in the case of a one-dimensional sensing region can have two points, for which the Hall-sensor gives the same Hall-voltage, such that the two points cannot be distinguished. In the case of a two-dimensional sensing region, the Hall-sensor can have a lot of points on a shared circle, for which the Hall-sensor can gives the same Hall-voltage and thus cannot be distinguished. The electrical resistance may be evaluated or measured by applying a voltage to the electrical resistance in one direction and by measuring a resulting electric current in the same direction. The electrical resistance may also be denoted as longitudinal electrical resistance. The position sensors may be arranged next or adjacent to each other along the transport plane, in particular such that the sensing regions of neighboring position sensors may not overlap or may overlap only partially, e.g. maximum ten percent in one dimension. From the known positons of the positions sensors below the transport plane and the evaluation of their electrical resistances and their values, respectively, the positions of the sample container carriers on top of the transport plane may be determined by the position determination unit.

According to an embodiment, the position sensor can comprise a spatially deflectable element. A spatial deflection of the spatially deflectable element can be dependent on the position of the sample container carrier located in the sensing region. The electrical resistance can be dependent on the spatial deflection. The spatial deflection may be along and/or substantially perpendicular to the transport plane. In particular, the spatially deflectable element may follow the sample container carrier along the transport plane and/or correspond to its position. The spatial deflection perpendicular to the transport plane may occur at and below, respectively, the position of the sample container carrier on the transport plane and not elsewhere. In particular, the spatially deflectable element may be deflected between at least two deflection states. When the sample container carrier is located out of the sensing region, no spatial deflection may occur, the spatially deflectable element may be deflected into a default deflection state and/or the spatially deflectable element may stay in its last state.

According to an embodiment, the spatially deflectable element can comprise a magnetic material. The magnetic material can be adapted to interact, or interacts, with the magnetically active device of the sample container carrier located in the sensing region, such that the spatial deflection can be caused. The magnetic material may comprise permanent magnetic material and/or magnetically soft material, in particular iron. Advantageously, the magnetically active device of the sample container carrier may be a permanent magnet and/or an electro-magnet, where the magnetic material can comprise magnetically soft material, or the magnetic material may comprise permanent magnetic material, where the magnetically active device of the sample container carrier can comprise magnetically soft material.

According to an embodiment, the spatially deflectable element can be embodied as a flexible membrane, in particular, extending along or substantially parallel to the transport plane. The flexible membrane may be spatially deflected substantially perpendicular to the transport plane. The use of the flexible membrane may ensure a relatively high reliability of the position sensor, since a relatively small and thereby relatively low-wear deflection of the flexible membrane may be sufficient to affect the electrical resistance.

According to an embodiment, the position sensor can have a given sensor length along the transport plane. The sensor length can define the sensing region. The electrical resistance can be dependent on the position of the sample container carrier on the transport plane located in the sensing region along the sensor length. In particular, the position sensor may comprise a housing and the sensor length may be defined by the housing.

According to an embodiment, the sensor length can be in the range from about 20 millimeter (mm) to about 60 mm. In one embodiment, the sensor length can be in the range from about 30 mm to about 50 mm. The sample container carrier may have a diameter on the transport plane and/or may have a footprint on the transport plane in this range. By the selection of this sensor length range, on the one hand, the sensor length may be relatively small enough to ensure, that only one sample container carrier may be located in the sensing region at a time. On the other hand, the sensor length may be relatively large enough to ensure, that a relatively low number of position sensors may be sufficient to capture the whole transport plane.

According to an embodiment, the position sensor can comprise a resistance element. The resistance element can extend over the sensor length along the transport plane. In addition, the position sensor can comprise a conductance element. The conductance element can be adapted to make a position-changeable electrical contact with the resistance element, such that the electrical resistance can be caused. A position of the electrical contact along the resistance element can be dependent on, in particular, can correspond to, the position of the sample container carrier, in particular on the transport plane located in the sensing region along the resistance element. The position-changeable electrical contact may be present permanently or only temporarily when the sample container carrier is located in the sensing region. Furthermore, the position sensor may comprise a first electrical contact element. The first electrical contact element may electrically contact the resistance element. Advantageously, the first electrical contact element may contact the resistance element at one end. The electrical resistance may be caused or established in between the conductance element and the first electrical contact element. This arrangement may also be denoted as variable resistor. In addition, the position sensor may comprise a second electrical contact element. The second electrical contact element may electrically contact the resistance element. Advantageously, the second electrical contact element may contact the resistance element at an opposite end than the first electrical contact element. A voltage may be applied in between the first electrical contact element and the second electrical contact element. A resulting voltage drop may be evaluated or measured in between the conductance element and the first electrical contact element. The voltage drop may be a measure for the electrical resistance. This arrangement may also be denoted as potentiometer or voltage divider. The conductance element may also be denoted as voltage tap.

According to an embodiment, the conductance element can extend over the sensor length along the transport plane, in particular, along the resistance element.

According to an embodiment, the spatially deflectable element can be formed by the resistance element and/or the conductance element. The spatial deflection of the spatially deflectable element can cause the position-changeable electrical contact. In particular, the resistance element and/or the conductance element may be embodied as the flexible membrane. Alternatively or additionally, the conductance element may be embodied as a sliding contact element, which may be adapted to slide along the resistance element.

According to an embodiment, the resistance element can extend in a first direction and in a second direction being different from the first direction. In addition, the position sensor can comprise a multiplexer for determination of the electrical resistance in the first direction and in the second direction. The multiplexer may enable to determine or to measure the electrical resistance in the first direction independent from the electrical resistance in the second direction. In particular, the first direction may be substantially perpendicular to the second direction. Furthermore, the position sensor may comprise for each direction an electrical contact element and optionally another electrical contact element.

According to an embodiment, the position sensors can be arranged in rows and columns. The rows and columns may form a grid or matrix. Furthermore, the grid of the position sensors may correspond or be aligned to a grid of the electro-magnetic actuators. Moreover, the position sensors may be arranged in a plane parallel to the transport plane.

According to an embodiment, the position sensors can be arranged in between the transport plane and the electro-magnetic actuators.

According to an embodiment, the laboratory sample distribution system can comprise a printed circuit board. The printed circuit board can be stationary arranged below the transport plane. The position sensor, in particular each of the position sensors, can be embodied as a surface-mount device and can be mounted directly onto a surface of the printed circuit board. Thereby, the position sensor/s may be easily installed or integrated below the transport plane.

According to an embodiment, the laboratory sample distribution system can comprise a control unit. The control unit can be in signal connection with the position determination unit. Also, the control unit can be configured to control the movements of the sample container carriers on top of the transport plane by driving the electro-magnetic actuators dependent on the positions of the sample container carriers on top of the transport plane such that the sample container carriers can move along corresponding transport paths.

Referring initially to FIG. 1, FIG. 1 shows a laboratory automation system 10. The laboratory automation system 10 can comprise a first laboratory station 20, a second laboratory station 30 and a laboratory sample distribution system 100. The laboratory automation system 10 can further comprises a gripping device 25, e.g. in the form of a pick-and-place device.

The laboratory sample distribution system 100 can comprise a transport plane 110. Under the transport plane 110, a plurality of electro-magnetic actuators 120 can be arranged in rows and columns. Each electro-magnetic actuator 120 can comprise a respective ferromagnetic core 125. A number of magnetic position sensors 130, embodied as Hall-sensors, can be distributed in rows and columns over the transport plane 110.

The laboratory sample distribution system 100 can further comprise a number of sample container carriers 140. A sample container carrier 140 can carry a respective sample container 145, embodied as laboratory sample tube. It is to be noted that only a single laboratory sample container carrier 140 carrying a respective sample container 145 is shown in FIG. 1 for exemplary purposes. A typical sample distribution system 100 can comprise a plurality of sample container carriers 140.

Each sample container carrier 140 can comprise a magnetically active device 141 in the form of a permanent magnet. Thus, magnetic fields generated by the electro-magnetic actuators 120 can drive a sample container carrier 140 over the transport plane 110. Further, the magnetic field generated by the permanent magnet 141 of a sample container carrier 140 can be detected by the position sensors 130, so that a feedback regarding the position of a sample container carrier 140 can be obtained.

Both the electro-magnetic actuators 120 and the position sensors 130 can be electrically connected to a control device 150. The control device 150 can drive the electro-magnetic actuators 120 such that the sample container carriers 140 can move along corresponding transport paths. The control device 150 can also determine the position of each sample container carrier 140.

The laboratory stations 20, 30 can be arranged adjacent to the transport plane 110. It is noted that these two laboratory stations 20, 30 are only shown for exemplary purposes in FIG. 1, and that a typical laboratory automation system 10 may comprise more than two laboratory stations 20, 30.

Adjacent to the first laboratory station 20, the gripping device 25 in the form of a robot arm is provided. The gripping device 25 can currently carry a position determining device 27 in the form of a pen held in a vertical orientation. The position determining device 27 can comprise a magnetically active device 28 in the form of a permanent magnet at its lower end.

Adjacent to the first laboratory station 20, a one of the electro-magnetic actuators 120 can be defined as a handover electro-magnetic actuator 121. If a sample container 145 is to be brought to or collected from the first laboratory station 20, a sample container carrier 140 carrying the specific sample container 145 can be moved to and then held by the handover electro-magnetic actuator 121. The sample container 145 can be gripped by the gripping device 25 and can then be handed over to the first laboratory station 20. The same principle can work basically in reverse order when a sample container 145 is to be collected from the first laboratory station 20 and is to be transported away by a sample container carrier 140.

When the first laboratory station 20 is placed adjacent to the laboratory sample distribution system 100 for the first time, the gripping device 25 can typically also be placed at its designated position. Then, the gripping device 25 can be calibrated so that it can grip a sample container 145 contained in a sample container carrier 140 that has been moved on the handover electro-magnetic actuator 121. This can be done using the position determining device 27, as will be explained below with respect to FIG. 2.

Figure 2:
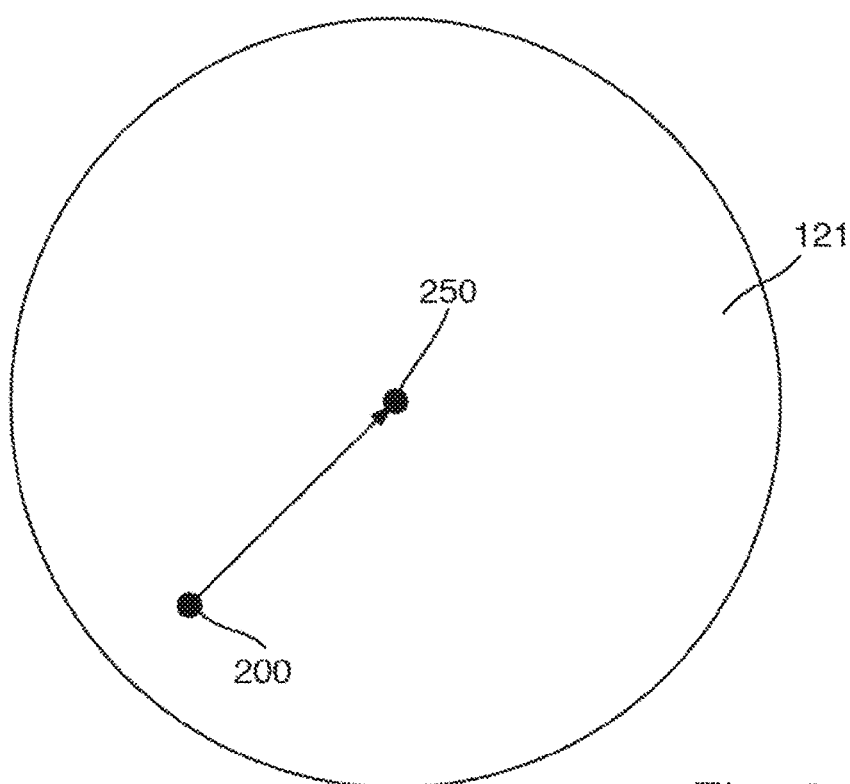
FIG. 2 illustrates a top view on a horizontal surface of a handover electro-magnetic actuator according to an embodiment of the present disclosure.

FIG. 2 shows a top view on the horizontal surface of the handover electro-magnetic actuator 121 for illustrating an embodiment that can be performed using the gripping device 25. It is to be understood that the method can be controlled by the control device 150, which can also take over the function of a process control unit. In other words, the control device 150 can also embody a process control unit.

At first, the position determining device 27 can be placed automatically at a starting position 200. This starting position 200 can subsequently be determined using the position sensors 130 that can be distributed over the transport plane 110. For that purpose, the position sensors may not only be able to binary detect presence or non-presence of a sample container carrier 140, but can be further adapted to provide a signal indicating a precise current magnetic field strength at the position of the respective position sensor 130.

For the purpose of determining the starting position 200 of the position determining device, the position sensors 130 adjacent to (or encircling) the handover electro-magnetic actuator 121 can be used. By the signals generated by these position sensors 130, the control device 150 can be able to exactly calculate the starting position 200.

In a typical implementation, it can be assumed that a handover position 250, i.e. the position at which the sample container carrier 140 can come to rest with its center when it is moved over the handover electro-magnetic actuator 121, can be defined at the center of the handover electro-magnetic actuator 121 (center position of the handover electro-magnetic actuator 121). This case is also shown in FIG. 2. Thus, the handover position 250 can, in the present case, be identical to the center position of the handover electro-magnetic actuator 121 in top view.

Knowing the starting position 200 and the handover position 250 in a Cartesian coordinate system of the transport plane 110, the control device 150 can then determine the difference between the two positions 200, 250 that is shown by a vector in FIG. 2. This difference can subsequently be used in order to calculate the handover position 250 in a Cartesian coordinate system of the gripping device 25. This can allow for a correction of the position at which the gripping device 25 can be placed, yielding a new starting position substantially identical to the handover position 250.

If the result of this process should be checked, the gripping device 25 can be operated to place the position determining device 27 at the newly determined starting position 200 and the position can be determined again. This can allow for a further determination of a correction, i.e. a refinement. Such refinements can be repeated e.g. until a desired accuracy is reached and/or a determined correction is less than a certain threshold.

If a sample container carrier 140 is moved to the handover electro-magnetic actuator 121, the gripping device can be moved to the determined handover position 250 and can thus grip correctly the sample container 145 contained in the sample container carrier 140.

Figure 3:
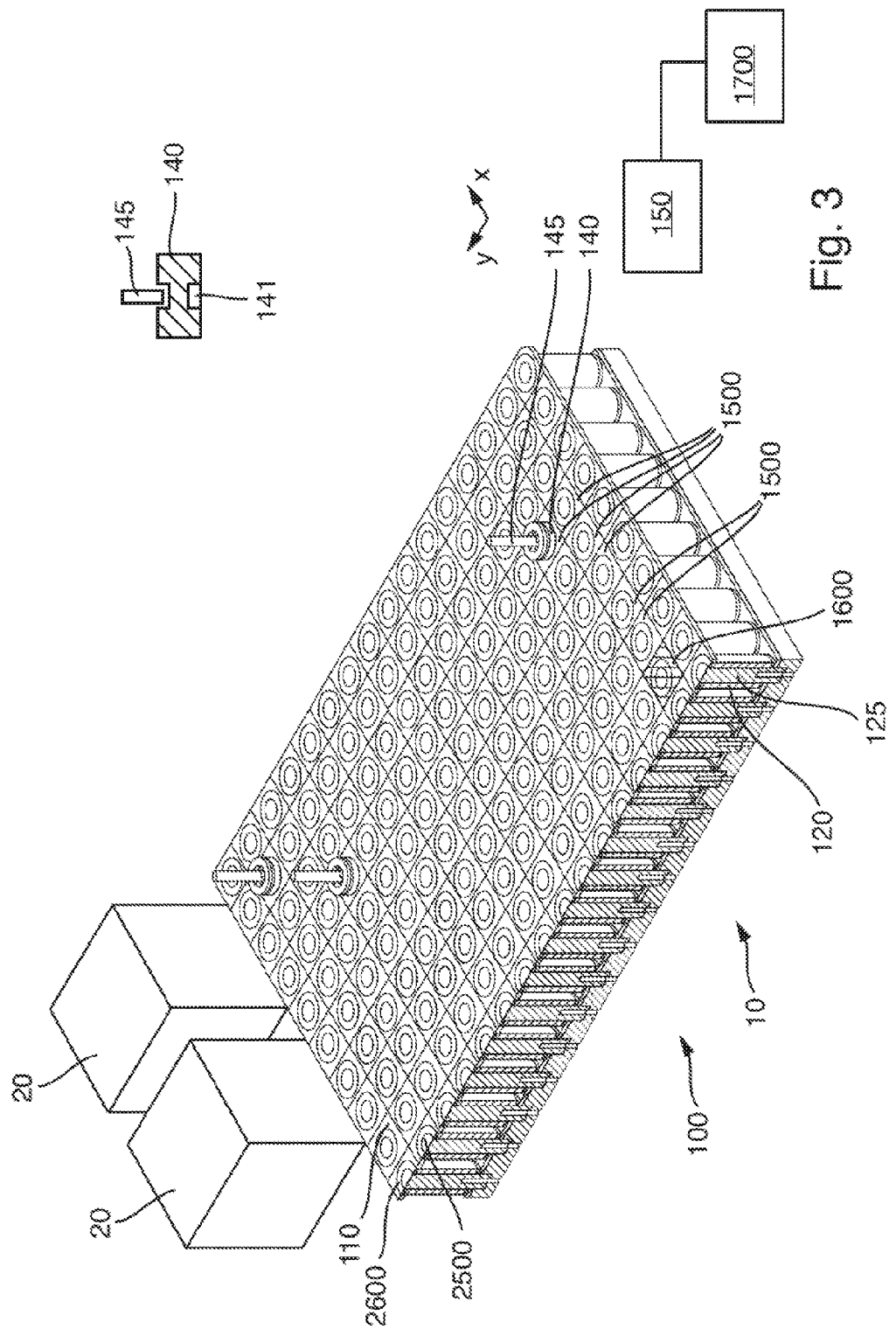
FIG. 3 illustrates a laboratory automation system according to another embodiment of the present disclosure.

FIG. 3 shows a laboratory automation system 10 comprising a laboratory sample distribution system 100 according to a further embodiment. The laboratory sample distribution system 100 can comprise a number of position sensors 1500 coupled to a position determination unit 1700. The position sensors 1500 may be used instead of or on conjunction with the position sensors 130 depicted in FIG. 1.

The position sensors 1500 can be stationary arranged below the transport plane 110. Each of the position sensors 1500 can have a sensing region 1600 and can have an electrical resistance Rx, Ry. The electrical resistance Rx, Ry, in particular a value of the electrical resistance Rx, Ry, can be dependent on a position PS of a sample container carrier 140 on the transport plane 110 located in the sensing region 1600 of a respective position sensor 1500. The position determination unit 1700 can be adapted to determine the positions PS of the sample container carriers 140 on top of the transport plane 110 by evaluating the electrical resistances Rx, Ry, in particular, the electrical resistance values, of the position sensors 1500.

In the shown embodiment, the sensing region 1600 of each position sensor 1500 can extend in two directions x, y being perpendicular to each other on the transport plane 110. In this case, the sensing region 1600 can comprise a sensing area on the transport plane 110. Furthermore, each of the position sensors 1500 can have an electrical resistance Rx and an electrical resistance value, respectively, for a first direction x and can have an electrical resistance Ry and an electrical resistance value, respectively, for a second direction y, as depicted in FIGS. 5b and 5c.

In detail, each of the position sensors 1500 can have a given sensor length Lx in the first direction x along the transport plane 110 and can have a given sensor length Ly in the second direction y along the transport plane 110, as depicted in FIGS. 4 and 5a. The sensor lengths Lx, Ly can define the sensing region 1600 of the respective position sensor 1500. The electrical resistance Rx in the first direction x can be dependent on the position PS of the sample container carrier 140 on the transport plane 110 located in the sensing region 1600 along the sensor length Lx. The electrical resistance Ry in the second direction y can be dependent on the position PS of the sample container carrier 140 on the transport plane 110 located in the sensing region 1600 along the sensor length Ly. In the shown embodiment, each of the sensor lengths Lx, Ly can be about 40 mm. These sensor lengths can correspond to a diameter of each sample container carrier 140 on the transport plane 110.

Further, the position sensor 1500 can comprise a resistance element 2100. The resistance element 2100 can extend over the sensor length Lx in the first direction x along or parallel to the transport plane 110 and can extend over the sensor length Ly in the second direction y along or parallel to the transport plane 110. In addition, the position sensor 1500 can comprise a conductance element 2200. The conductance element 2200 can be adapted to make a position-changeable electrical contact 2300 with the resistance element 2100, such that the electrical resistances Rx, Ry can be caused. A position PC of the electrical contact 2300 along the resistance element 2100 can be dependent on the position PS of the sample container carrier 140 on the transport plane 110 located in the sensing region 1600 along the resistance element 2100.

Also, the position sensor 1500 can comprise a spatially deflectable element 1900. A spatial deflection of the spatially deflectable element 1900 can be dependent on the position PS of the sample container carrier 140 located in the sensing region 1600. The electrical resistances Rx, Ry can be dependent on the spatial deflection.

In the shown embodiment, the spatially deflectable element 1900 can be formed by the conductance element 2200. The spatial deflection of the spatially deflectable element 1900 can cause the position-changeable electrical contact 2300. The spatially deflectable element 1900 and the conductance element 2200, respectively, can be embodied as a flexible membrane. The conductance element 2200 can extend over the sensor length Lx in the first direction x along or parallel to the transport plane 110 and the resistance element 2100 and can extend over the sensor length Ly in the second direction y along or parallel to the transport plane 110 and the resistance element 2100.

The position sensor 1500 can comprise a housing 2900. The resistance element 2100 and the conductance element 2200 can be arranged inside of the housing 2900 parallel to each other separated by an air gap. The housing 2900 can be arranged below the transport plane 110 with the resistance element 2100 being closer to the transport plane 110 than the conductance element 2200. The as the flexible membrane embodied conductance element 2200 can be fixed or clamped at its border or edge to the housing 2900.

The spatially deflectable element 1900 and the conductance element 2200, respectively, can comprise a magnetic material 2000. The magnetic material 2000 can be adapted to interact or interacts with the magnetically active device 141 of the sample container carrier 140 located in the sensing region 1600, such that the spatial deflection can be caused. In the shown embodiment, the magnetic material 2000 can comprise magnetically soft material in the form of iron beads, wherein the iron beads can be integrated into the flexible membrane.

In other embodiments, the spatially deflectable element may be formed by the resistance element. In particular, the resistance element may be embodied as a flexible membrane. Furthermore, a housing may be arranged with the conductance element closer to the transport plane than the resistance element. Moreover, the resistance element may comprise a magnetic material. The magnetic material may be adapted to interact or may interact with the magnetically active device of the sample container carrier located in the sensing region, such that a spatial deflection of the resistance element may be caused and the position-changeable electrical contact with the conductance element may be made.

In the shown embodiment, a magnetic strength of both, the magnetically active device 141 of the sample container carrier 140 and the magnetic material 2000 of the spatially deflectable element 1900, can be chosen such that the magnetic material 2000 can be attracted by the magnetically active device 141 such that the conductance element 2200 can be spatially deflected substantially perpendicular to the transport plane 110 towards the resistance element 2100 into electrical contact with it, when the sample container carrier 140 on the transport plane 110 is located in the sensing region 1600 of the position sensor 1500. The spatial deflection can occur at and below, respectively, the position PS of the sample container carrier 140 on the transport plane 110 and not elsewhere. Thereby, the position-changeable electrical contact 2300 can be made at the position PC, which can corresponds to the position PS of the sample container carrier 140. The spatially deflectable element can be in a first deflection state or electrical contact deflection state.

In detail, the resistance element 2100 can comprise a resistance material, which can be uniform along the sensor lengths Lx, Ly. The position sensor 1500 can comprise a first electrical contact element 2360. The first electrical contact element 2360 can electrically contact the resistance element 2100 at an end, in FIG. 5a on the left. The electrical resistance Rx in the first direction x can be caused in between the first electrical contact element 2360 and the conductance element 2200 with its position-changeable electrical contact 2300. In addition, the position sensor 1500 can comprise a conductance contact element 2350. The conductance contact element 2350 can electrically contact the conductance element 2200. The conductance element 2200 can comprise a conductance material. An electrical resistance of the conductance element 2200 and an electrical resistivity of the conductance material, respectively, can be negligibly or insignificantly small compared to an electrical resistance of the resistance element 2100 and to an electrical resistivity of the resistance material, respectively. Thereby, an electrical resistance in between the conductance contact element 2350 and the position-changeable electrical contact 2300 can be negligibly or insignificantly small compared to the electrical resistance Rx. In addition, the position sensor 1500 can comprise a second electrical contact element 2380. The second electrical contact element 2380 can electrically contact the resistance element 2100 at an opposite end than the first electrical contact element 2360, in FIG. 5a on the right. A given voltage can be applied in between the first electrical contact element 2360 and the second electrical contact element 2380, e.g. 3.3 Volts (V), in particular in the first direction x. A resulting voltage drop can be evaluated or measured analog in between the conductance contact element 2350 and the first electrical contact element 2360, in particular in the first direction x. The evaluated voltage drop can be a measure for the electrical resistance Rx in the first direction x. This arrangement may also be denoted as potentiometer. The conductance element 2200 may also be denoted as voltage tap. The electrical resistance Rx may also be denoted as longitudinal electrical resistance.

The position sensor 1500 can comprise a third electrical contact element 2370. The third electrical contact element 2370 can electrically contact the resistance element 2100 at an end, in FIG. 5a on the bottom. The electrical resistance Ry in the second direction y can be caused in between the second electrical contact element 2370 and the conductance element 2200 with its position-changeable electrical contact 2300. An electrical resistance in between the conductance contact element 2350 and the position-changeable electrical contact 2300 can be negligibly small compared to the electrical resistance Ry. In addition, the position sensor 1500 can comprise a fourth electrical contact element 2390. The fourth electrical contact element 2390 can electrically contact the resistance element 2100 at an opposite end than the third electrical contact element 2370, in FIG. 5a on the top. The given voltage can be applied in between the third electrical contact element 2370 and the fourth electrical contact element 2390. A resulting voltage drop can be evaluated analog in between the conductance contact element 2350 and the third electrical contact element 2370. The evaluated voltage drop can be a measure for the electrical resistance Ry in the second direction y. The electrical resistance Ry may also be denoted as longitudinal electrical resistance.

The position sensor 1500 can comprise a multiplexer 2400 for determination of the electrical resistance Rx, Ry in the first direction x and in the second direction y. Firstly, the given voltage can be applied in between the first electrical contact element 2360 and the second electrical contact element 2380 by the multiplexer 2400 and the electrical resistance Rx can be determined, while no voltage is applied in between the third electrical contact element 2370 and the fourth electrical contact element 2390. Secondly, the given voltage can be applied in between the third electrical contact element 2370 and the fourth electrical contact element 2390 by the multiplexer 2400 and the electrical resistance Ry can be determined, while no voltage is applied in between the first electrical contact element 2360 and the second electrical contact element 2380. Thereby, the multiplexer 2400 can determine or measure the electrical resistance Rx in the first direction x independent from the electrical resistance Ry in the second direction y.

The electrical resistances Rx, Ry can be unambiguously assigned to the position PS of the sample container carrier 140 on the transport plane 110 located in the sensing region 1600 of the respective position sensor 1500. The electrical resistance Rx in the first direction x can increase with the position-changeable electrical contact 2300 moving from the left to the right in FIG. 5a. The electrical resistance Ry in the second direction y can increase with the position-changeable electrical contact 2300 moving from the bottom to the top in FIG. 5a. For the position PS of the sample container carrier 140 shown in FIGS. 4 and 5, the electrical resistance Rx can be larger than the electrical resistance Ry and both can be almost at maximum. Hence, the position PS of the sample container carrier 140 located in the sensing region 1600 of the respective position sensor 1500 can be unambiguously determined by the position determination unit 1700. When the sample container carrier 140 is located outside of the sensing region 1600 of the respective position sensor 1500, no spatial deflection of the spatially deflectable element 1900 and the conductance element 2200, respectively, can occur. The spatially deflectable element 1900 can be in a second deflection state or default deflection state. The position-changeable electrical contact 2300 may not be present. In this case, the electrical resistances Rx, Ry can each have an extreme value.

As depicted in FIG. 3, the position sensors 1500 can be arranged in rows 2500 and columns 2600, in particular, quadratically. The rows and columns can form a grid. Furthermore, the grid of the position sensors 1500 can correspond or can be aligned to the grid of the electro-magnetic actuators 120. The sensing regions 1600 of neighboring position sensors 1500 may not overlap, but can be seamlessly adjoined. Thereby, the whole transport plane 110 can be captured. From the known positons of the positions sensors 1500 below the transport plane 110 and the evaluation of their electrical resistances Rx, Ry, the positions PS of the sample container carriers 140 on top of the transport plane 110 can be determined by the position determination unit 1700.

Moreover, the position sensors 1500 can be arranged in between the transport plane 110 and the electro-magnetic actuators 120, in particular in a plane parallel to the transport plane 110, as depicted in FIG. 6.

Further, the laboratory sample distribution system 100 can comprise a printed circuit board 2700. The printed circuit board 2700 can be stationary arranged below the transport plane 110. Each of the position sensors 1500 can be embodied as a surface-mount device and can be mounted directly onto a surface 2800 of the printed circuit board 2700.

In addition, the laboratory sample distribution system 100 can comprise the control unit 150, as already depicted in FIG. 1. The control unit 150 can be in signal connection with the position determination unit 1700. In addition, the control unit 150 can be configured to control the movements of the sample container carriers 140 on top of the transport plane 110 by driving the electro-magnetic actuators 120 dependent on the positions PS of the sample container carriers 140 on top of the transport plane 110 such that the sample container carriers 140 can independently and simultaneously move along the transport paths. The position sensors and the position determination unit can enable improved sample container carrier position detection on the transport plane. The first position and/or the second position may be determined by the position sensors 1500.

It is noted that terms like "preferably," "commonly," and "typically" are not utilized herein to limit the scope of the claimed embodiments or to imply that certain features are critical, essential, or even important to the structure or function of the claimed embodiments. Rather, these terms are merely intended to highlight alternative or additional features that may or may not be utilized in a particular embodiment of the present disclosure.

For the purposes of describing and defining the present disclosure, it is noted that the term "substantially" is utilized herein to represent the inherent degree of uncertainty that may be attributed to any quantitative comparison, value, measurement, or other representation. The term "substantially" is also utilized herein to represent the degree by which a quantitative representation may vary from a stated reference without resulting in a change in the basic function of the subject matter at issue.

Having described the present disclosure in detail and by reference to specific embodiments thereof, it will be apparent that modifications and variations are possible without departing from the scope of the disclosure defined in the appended claims. More specifically, although some aspects of the present disclosure are identified herein as preferred or particularly advantageous, it is contemplated that the present disclosure is not necessarily limited to these preferred aspects of the disclosure.

I claim:

1. A method of setting a handover position of a gripping device, wherein the gripping device is assigned to a laboratory sample distribution system having a transport plane, a number of electro-magnetic actuators positioned below the transport plane and a number of position sensors distributed over the transport plane and wherein the handover position is assigned to a handover electro-magnetic actuator, the method comprising:

gripping, by the gripping device, a position determining device such that the position determining device is held fixedly by the gripping device, wherein the position determining device comprises a magnetically active device;

positioning the position determining device, while held by the gripping device, on the transport plane;

detecting a first position of the position determining device on the transport plane using the position sensors; and setting the handover position based at least in part on the first position.

2. The method according to claim 1, wherein the handover position is represented in a coordinate system of the gripping device.

3. The method according to claim 1, wherein the handover position is calculated based on a difference between the first position and a center position of the handover electro-magnetic actuator.

4. The method according to claim 1, wherein the position sensors are configured to measure a quantitative strength of a magnetic field generated by the magnetically active device.

5. The method according to claim 4, wherein the first position is determined based on the measured strengths of the magnetic field.

6. The method according to claim 1, wherein when detecting the first position, position sensors surrounding the handover electro-magnetic actuator are used.

7. The method according to claim 1, wherein the electro-magnetic actuators are deactivated while performing the method.

8. The method according to claim 1, wherein the first position and/or the center position are represented by planar coordinates on the transport plane.

9. The method according to claim 1, wherein the step of positioning, by the gripping device, the position determining device on the transport plane is performed such that the gripping device is positioned over or besides the handover electro-magnetic actuator.

10. The method according to claim 1, wherein the step of positioning the position determining device, while held by the gripping device, on the transport plane is performed automatically.

11. The method according to claim 1, wherein after determining the handover position, the method further comprises, positioning the position determining device, while held by the gripping device, on the transport plane at the handover position;

detecting a second position of the position determining device on the transport plane using the position sensors; and refining the handover position based at least in part on the second position.

12. A laboratory automation system, the laboratory automation system comprising:

a number of gripping devices;

a position determining device fixedly held by at last one of the number of gripping devices;

a laboratory sample distribution system, the laboratory sample distribution system comprising, a number of sample container carriers adapted to carry one or more sample containers, each sample container carrier comprising at least one magnetically active device, a transport plane adapted to support the sample container carriers, a number of electro-magnetic actuators stationary arranged below the transport plane, the electro-magnetic actuators adapted to move a sample container carrier on top of the transport plane by applying a magnetic force to the sample container carrier, and a control device configured to control the movement of the sample container carriers on top of the transport plane by driving the electro-magnetic actuators such that the sample container carriers move along corresponding transport paths, wherein for each gripping device, a handover electro-magnetic actuator is assigned the number of electro-magnetic actuators, wherein a sample container is to be handed over to or from the gripping device while a sample container carrier carrying the respective sample container is positioned above the handover electro-magnetic actuator; and a process control unit, wherein the process control unit is configured to control the gripping devices and the laboratory sample distribution system such that the method according to claim 1 is performed.

13. The laboratory automation system according to claim 12, further comprises, a number of laboratory stations.

14. The laboratory automation system according to claim 12, wherein the magnetically active device of the position determining device generates a stronger magnetic field than each of the magnetically active devices of the sample container carriers.

* * * * *